(12) United States Patent
Hata et al.

(10) Patent No.: US 11,395,694 B2
(45) Date of Patent: Jul. 26, 2022

(54) IRRIGATED ABLATION CATHETER WITH MULTIPLE SEGMENTED ABLATION ELECTRODES

(75) Inventors: Cary Hata, Irvine, CA (US); Thu Xuan Tran, Garden Grove, CA (US); Alan de la Rama, Cerritos, CA (US); Tho Hoang Nguyen, Huntington Beach, CA (US); Irvin John Narciso, Rancho Santa Margarita, CA (US); Peter C. Chen, Irvine, CA (US); Hanh Ngoc Do, Garden Grove, CA (US)

(73) Assignee: ST. JUDE MEDICAL, LLC, Abbott Park, IL (US)

( * ) Notice: Subject to any disclaimer, the term of this patent is extended or adjusted under 35 U.S.C. 154(b) by 508 days.

(21) Appl. No.: 12/436,977

(22) Filed: May 7, 2009

(65) Prior Publication Data

US 2010/0286684 A1 Nov. 11, 2010

(51) Int. Cl.
*A61B 18/14* (2006.01)
*A61B 17/00* (2006.01)
*A61B 18/00* (2006.01)

(52) U.S. Cl.
CPC .... *A61B 18/1492* (2013.01); *A61B 2017/003* (2013.01); *A61B 2017/00867* (2013.01);
(Continued)

(58) Field of Classification Search
CPC ...... A61B 18/1492; A61B 2018/00029; A61B 2018/1467; A61B 2018/1465;
(Continued)

(56) References Cited

U.S. PATENT DOCUMENTS

| 4,325,374 A | 4/1982 | Komiya |
| 5,279,299 A | 1/1994 | Imran |

(Continued)

FOREIGN PATENT DOCUMENTS

| CN | 1897885 A | 1/2007 |
| JP | 2002513652 A | 5/2002 |

(Continued)

OTHER PUBLICATIONS

PCT International Search Report (PCT/US2008/069248), dated Jan. 15, 2009, 2 pages.

(Continued)

*Primary Examiner* — Deanna K Hall
(74) *Attorney, Agent, or Firm* — Armstrong Teasdale LLP

(57) ABSTRACT

In one embodiment, an irrigated catheter ablation apparatus comprises an elongated body having a distal end, a proximal end, and at least one fluid lumen extending longitudinally therein; and a plurality of segmented ablation electrodes on a distal portion of the elongated body. The electrodes are spaced from the proximal end and from the distal end of the elongated body by electrically nonconductive segments. The electrodes are spaced from each other longitudinally by electrically nonconductive segments. For each electrode that is longitudinally disposed next to one of the nonconductive segments, an edge is formed between an electrode end of the electrode and a nonconductive segment end of the nonconductive segment. A plurality of elution holes are disposed adjacent to the edges. A plurality of ducts establish fluid communication between the elution holes and the fluid lumen.

26 Claims, 17 Drawing Sheets

(52) U.S. Cl.
CPC .............. *A61B 2018/00029* (2013.01); *A61B 2018/00404* (2013.01); *A61B 2018/00434* (2013.01); *A61B 2018/00511* (2013.01); *A61B 2018/00839* (2013.01); *A61B 2018/1467* (2013.01); *A61B 2218/002* (2013.01); *C08L 2201/12* (2013.01)

(58) Field of Classification Search
CPC ....... A61B 2018/00577; A61B 2218/001–002; A61B 2218/00577; A61M 25/0013; A61M 25/0054
USPC ............. 604/32, 34, 41; 606/33, 41, 47, 129
See application file for complete search history.

(56) References Cited

U.S. PATENT DOCUMENTS

| | | | |
|---|---|---|---|
| 5,364,352 A | 11/1994 | Cimino et al. | |
| 5,378,230 A | 1/1995 | Mahurkar | |
| 5,462,521 A | 10/1995 | Brucker et al. | |
| 5,487,385 A | 1/1996 | Avitall | |
| 5,520,682 A | 5/1996 | Baust et al. | |
| 5,545,200 A | 8/1996 | West et al. | |
| 5,569,220 A | 10/1996 | Webster, Jr. | |
| 5,643,197 A | 7/1997 | Brucker et al. | |
| 5,772,642 A | 6/1998 | Ciamacco, Jr. et al. | |
| 5,800,428 A | 9/1998 | Nelson et al. | |
| 5,810,802 A * | 9/1998 | Panescu ............... | A61B 5/0422 374/E1.005 |
| 5,833,632 A | 11/1998 | Jacobsen et al. | |
| 5,853,425 A | 12/1998 | Houser | |
| 5,893,885 A * | 4/1999 | Webster, Jr. ....... | A61B 18/1492 607/122 |
| 5,919,188 A | 7/1999 | Shearon et al. | |
| 5,951,471 A | 9/1999 | de la Rama et al. | |
| 5,954,719 A | 9/1999 | Chen et al. | |
| 5,992,418 A | 11/1999 | de la Rama et al. | |
| 6,001,095 A | 12/1999 | de la Rama et al. | |
| 6,010,500 A * | 1/2000 | Sherman et al. ................ | 606/41 |
| 6,030,382 A | 2/2000 | Fleischman et al. | |
| 6,063,080 A | 5/2000 | Nelson et al. | |
| 6,210,409 B1 | 4/2001 | Ellman et al. | |
| 6,217,573 B1 | 4/2001 | Webster | |
| 6,233,476 B1 | 5/2001 | Strommer et al. | |
| 6,235,022 B1 | 5/2001 | Hallock et al. | |
| 6,251,134 B1 | 6/2001 | Alt et al. | |
| 6,273,876 B1 | 8/2001 | Klima et al. | |
| 6,308,090 B1 | 10/2001 | Tu et al. | |
| 6,325,797 B1 | 12/2001 | Stewart et al. | |
| 6,332,880 B1 * | 12/2001 | Yang ................. | A61M 25/0043 604/528 |
| 6,346,104 B2 | 2/2002 | Daly et al. | |
| 6,356,790 B1 | 3/2002 | Maguire et al. | |
| 6,379,349 B1 | 4/2002 | Mueller et al. | |
| 6,405,067 B1 | 6/2002 | Mest et al. | |
| 6,464,632 B1 | 10/2002 | Taylor | |
| 6,493,590 B1 | 12/2002 | Wessman et al. | |
| 6,498,944 B1 | 12/2002 | Ben-Haim et al. | |
| 6,522,930 B1 | 2/2003 | Schaer et al. | |
| 6,604,003 B2 | 8/2003 | Fredricks et al. | |
| 6,611,699 B2 | 8/2003 | Messing | |
| 6,690,963 B2 | 2/2004 | Ben-Haim et al. | |
| 6,780,183 B2 | 8/2004 | Jimenez, Jr. et al. | |
| 6,788,967 B2 | 9/2004 | Ben-Haim et al. | |
| 6,921,397 B2 | 7/2005 | Corcoran et al. | |
| 6,980,843 B2 | 12/2005 | Eng et al. | |
| 7,013,169 B2 | 3/2006 | Bowe | |
| 7,137,395 B2 | 11/2006 | Fried et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,389,148 B1 * | 6/2008 | Morgan ................. | A61N 1/056 600/372 |
| 7,416,552 B2 | 8/2008 | Paul et al. | |
| 7,468,027 B2 | 12/2008 | Barbut et al. | |
| 7,536,218 B2 | 5/2009 | Govari et al. | |
| 7,537,595 B2 | 5/2009 | McClurken | |
| 7,565,208 B2 | 7/2009 | Harris et al. | |
| 7,669,309 B2 | 3/2010 | Johnson et al. | |
| 7,699,771 B2 | 4/2010 | Wendlandt et al. | |
| 7,706,891 B2 | 4/2010 | Hastings et al. | |
| 7,824,517 B2 | 11/2010 | Kampa et al. | |
| 7,826,881 B1 | 11/2010 | Beatty et al. | |
| 2001/0007070 A1 * | 7/2001 | Stewart ............. | A61B 18/1492 606/41 |
| 2001/0012956 A1 | 8/2001 | Behl et al. | |
| 2002/0058866 A1 | 5/2002 | Segner et al. | |
| 2002/0072710 A1 | 6/2002 | Stewart et al. | |
| 2003/0125730 A1 | 7/2003 | Berube et al. | |
| 2004/0015215 A1 | 1/2004 | Fredricks et al. | |
| 2004/0034348 A1 | 2/2004 | Rashidi | |
| 2004/0064158 A1 | 4/2004 | Klein et al. | |
| 2004/0143256 A1 | 7/2004 | Bednarek | |
| 2004/0193239 A1 * | 9/2004 | Falwell .............. | A61B 18/1492 607/122 |
| 2004/0204671 A1 | 10/2004 | Stubbs et al. | |
| 2004/0220461 A1 | 11/2004 | Schwartz | |
| 2004/0231683 A1 | 11/2004 | Eng et al. | |
| 2004/0243143 A1 | 12/2004 | Corcoran et al. | |
| 2004/0267106 A1 | 12/2004 | Segner et al. | |
| 2005/0004563 A1 | 1/2005 | Racz et al. | |
| 2005/0043713 A1 | 2/2005 | Zhou | |
| 2005/0054989 A1 | 3/2005 | McGuckin, Jr. et al. | |
| 2005/0070894 A1 | 3/2005 | McClurken | |
| 2005/0143729 A1 | 6/2005 | Francischelli et al. | |
| 2005/0187561 A1 | 8/2005 | Lee-Sepsick et al. | |
| 2005/0197633 A1 | 9/2005 | Schwartz et al. | |
| 2005/0272975 A1 | 12/2005 | McWeeney et al. | |
| 2006/0004353 A1 | 1/2006 | Koyfman et al. | |
| 2006/0064123 A1 | 3/2006 | Bonnette et al. | |
| 2006/0149192 A1 | 7/2006 | Deniega et al. | |
| 2006/0200191 A1 | 9/2006 | Zadno-Azizi | |
| 2006/0287650 A1 | 12/2006 | Cao et al. | |
| 2007/0005053 A1 | 1/2007 | Dando | |
| 2007/0156114 A1 | 7/2007 | Worley et al. | |
| 2007/0179491 A1 | 8/2007 | Kratoska et al. | |
| 2007/0299424 A1 | 12/2007 | Cumming et al. | |
| 2008/0091195 A1 | 4/2008 | Sliwa et al. | |
| 2008/0125772 A1 | 5/2008 | Stone et al. | |
| 2008/0139999 A1 | 6/2008 | Gibson et al. | |
| 2008/0161788 A1 | 7/2008 | Dando et al. | |
| 2008/0161789 A1 | 7/2008 | Chou et al. | |
| 2008/0249522 A1 * | 10/2008 | Pappone ................. | A61B 18/18 606/41 |
| 2008/0275428 A1 | 11/2008 | Tegg et al. | |
| 2008/0281319 A1 | 11/2008 | Paul et al. | |
| 2008/0294158 A1 * | 11/2008 | Pappone ............ | A61B 18/1492 606/41 |
| 2008/0300589 A1 | 12/2008 | Paul et al. | |
| 2008/0312713 A1 | 12/2008 | Wilfley et al. | |
| 2009/0012517 A1 | 1/2009 | de la Rama et al. | |
| 2009/0228092 A1 | 9/2009 | Raeder-Devens et al. | |
| 2009/0247993 A1 | 10/2009 | Kirschenman et al. | |
| 2009/0287210 A1 | 11/2009 | Kauphusman et al. | |
| 2010/0152731 A1 | 6/2010 | De La Rama et al. | |
| 2010/0174177 A1 | 7/2010 | Wu | |
| 2011/0118582 A1 | 5/2011 | De La Rama et al. | |

FOREIGN PATENT DOCUMENTS

| | | |
|---|---|---|
| JP | 2006509547 A | 3/2006 |
| JP | 2008136875 A | 6/2008 |
| JP | 2008541799 A | 11/2008 |
| JP | 3162588 U | 9/2010 |
| JP | 2010533564 A | 10/2010 |
| WO | 9510327 A1 | 4/1995 |
| WO | 1996034652 A1 | 11/1996 |
| WO | 9717904 A1 | 5/1997 |
| WO | 1999/056812 | 11/1999 |
| WO | 02087453 A1 | 11/2002 |
| WO | 2005094661 A1 | 10/2005 |
| WO | 2007035554 A1 | 3/2007 |
| WO | 2008/124619 | 10/2008 |

(56) References Cited

FOREIGN PATENT DOCUMENTS

| WO | 2008147599 | A1 | 12/2008 |
| WO | 2009120982 | A2 | 10/2009 |
| WO | 2010129661 | A1 | 11/2010 |

OTHER PUBLICATIONS

International Search Report and Written Opinion, PCT/US2011/040781 dated Nov. 25, 2011.
International Search Report and Written Opinion, PCT/US2011/046266 dated Dec. 7, 2011.

\* cited by examiner

IRRIGATED ABLATION CATHETER WITH MULTIPLE SEGMENTED ABLATION ELECTRODES

BACKGROUND OF THE INVENTION

The present invention relates generally to catheter devices, and more specifically to irrigated catheter devices with multiple segmented ablation segments.

Catheters are flexible, tubular devices that are widely used by physicians performing medical procedures to gain access into interior regions of the body. Certain types of catheters are commonly referred to as irrigated catheters that deliver fluid to a target site in an interior region of the body. Such irrigated catheters may deliver various types of fluid to the patient, including, for example, medications, therapeutic fluids, and even cooling fluids for certain procedures wherein heat is generated within targeted areas of the body.

For example, ablation catheters are sometimes used to perform ablation procedures to treat certain conditions of a patient. A patient experiencing arrhythmia, for example, may benefit from ablation to prevent irregular heart beats caused by arrhythmogenic electrical signals generated in cardiac tissues. By ablating or altering cardiac tissues that generate such unintended electrical signals the irregular heart beats may be stopped. Ablation catheters are known, and may include one or more ablation electrodes supplying RF (radiofrequency) energy to targeted tissue. With the aid of sensing and mapping tools that are also known, an electrophysiologist can determine a region of tissue in the body, such as cardiac tissue, that may benefit from ablation.

Once tissue is targeted for ablation, a catheter tip having one or more ablation electrodes may be positioned over the targeted tissue. The ablation electrodes may deliver RF energy, for example, supplied from a generator, to create sufficient heat to damage the targeted tissue. By damaging and scarring the targeted tissue, aberrant electrical signal generation or transmission may be interrupted. In some instances irrigation features may be provided in ablation catheters to supply cooling fluid in the vicinity of the ablation electrodes to prevent overheating of tissue and/or the ablation electrodes. There are typically two classes of irrigated catheter devices, open and closed ablation catheters. Closed ablation catheters typically circulate a cooling fluid within the inner cavity of the ablation catheter tip. Open ablation catheters, on the other hand, use the inner cavity of the ablation catheter tip as a manifold to distribute saline solution, or other irrigation fluids known to those skilled in the art, to one or more passageways leading to an orifice. This lowers the temperature of the ablation catheter tip by bringing the outer surface of the ablation electrode in contact with the cool irrigation fluid and dilute the blood around the electrode to prevent blood coagulation.

BRIEF SUMMARY OF THE INVENTION

Exemplary embodiments of the invention provide an irrigated catheter ablation apparatus with multiple segmented ablation segments.

In accordance with an aspect of the present invention, an irrigated catheter ablation apparatus comprises an elongated body having a distal end, a proximal end, and at least one fluid lumen extending longitudinally therein; and a plurality of segmented ablation electrodes on a distal portion of the elongated body. The plurality of segmented ablation electrodes are spaced from the proximal end and from the distal end of the elongated body by electrically nonconductive segments. The plurality of segmented ablation electrodes are spaced from each other longitudinally by electrically nonconductive segments. For each segmented ablation electrode that is longitudinally disposed next to one of the electrically nonconductive segments, an edge is formed between an electrode end of the segmented ablation electrode and a nonconductive segment end of the electrically nonconductive segment. A plurality of elution holes are disposed adjacent to the edges which are between the electrode ends of the segmented ablation electrodes and the nonconductive segment ends of the electrically nonconductive segments. A plurality of ducts establish fluid communication between the elution holes and the at least one fluid lumen.

In some embodiments, the plurality of elution holes may be disposed in the plurality of electrically nonconductive segments. The plurality of elution holes may be disposed in the plurality of segmented ablation electrodes. The plurality of segmented ablation electrodes may include at least one of a coil ring electrode having gaps in a coil to permit fluid flow therethrough or a ring electrode having gaps cut into the ring electrode to permit fluid flow therethrough. For each of the edges, at least one of the elution holes is disposed adjacent the edge. For each of the edges, more than one of the elution holes are spaced around a circumference adjacent the edge.

In specific embodiments, a tip electrode is disposed at the distal end of the elongated body. The tip electrode has a proximal end which meets a nonconductive segment end of one of the electrically nonconductive segments at a tip electrode edge. At least one tip electrode edge elution hole is disposed adjacent to the tip electrode edge and being in fluid communication with the at least one fluid lumen. The tip electrode may be an ablation tip electrode. The at least one tip electrode edge elution hole is disposed in the tip electrode. At least some of the ducts are substantially perpendicular to the at least one fluid lumen. The distal portion of the elongated body includes a material which is preformed into a substantially closed loop having the plurality of longitudinally spaced segmented ablation electrodes and the electrically nonconductive segments.

In some embodiments, one or more conducting wires coupled with and supplying RF energy to the plurality of segmented ablation electrodes, the RF energy being one of unipolar RF energy or bipolar RF energy. One or more conducting wires are coupled with the plurality of segmented ablation electrodes. An energy source supplies energy via the one or more conducting wires to the plurality of segmented ablation electrodes. A controller is configured to control the energy source to supply energy to the plurality of segmented ablation electrodes in one of an independent manner, a sequential manner, or a simultaneous manner.

In specific embodiments, a plurality of temperature sensors are disposed on and in contact with the plurality of segmented ablation electrodes at the electrode ends. The temperature sensors each substantially abut the edge between one of the electrode ends of the segmented ablation electrodes and one of the nonconductive segment ends of the electrically nonconductive segments. In another embodiment, each of a plurality of temperature sensors is disposed on and in contact with a respective segmented ablation electrode at a location situated between the electrode ends. A controller is configured to control the energy source to supply energy to the plurality of segmented ablation electrodes based on signals received from the plurality of temperature sensors so as to control temperatures of the plurality of segmented ablation electrodes.

In accordance with another aspect of the invention, a method of ablating tissue with an irrigated catheter comprises directing fluid through a plurality of elution holes disposed adjacent to the edges which are between the electrode ends of the segmented ablation electrodes and the nonconductive segment ends of the electrically nonconductive segments; and supplying energy to the plurality of segmented ablation electrodes to ablate tissue.

In some embodiments, the distal portion of the elongated body includes a material which is preformed into a substantially closed loop having the plurality of longitudinally spaced segmented ablation electrodes and the electrically nonconductive segments. The substantially closed loop is placed around at least one vessel ostium in a chamber of a patient to ablate the tissue on a chamber wall of the chamber around the at least one vessel ostium. The at least one vessel ostium comprises at least one pulmonary vein. The substantially closed loop may be placed within a vessel of a patient to denervate nerves within and around a vessel wall of the vessel. Denervation is defined herein as partially or totally blocking nerve conduction. Denervation may be achieved by stimulating, or overstimulating, or ablating the nerves. The vessel comprises a renal artery or a renal vein.

These and other features and advantages of the present invention will become apparent to those of ordinary skill in the art in view of the following detailed description of the specific embodiments.

DETAILED DESCRIPTION OF THE INVENTION

Figure 1:
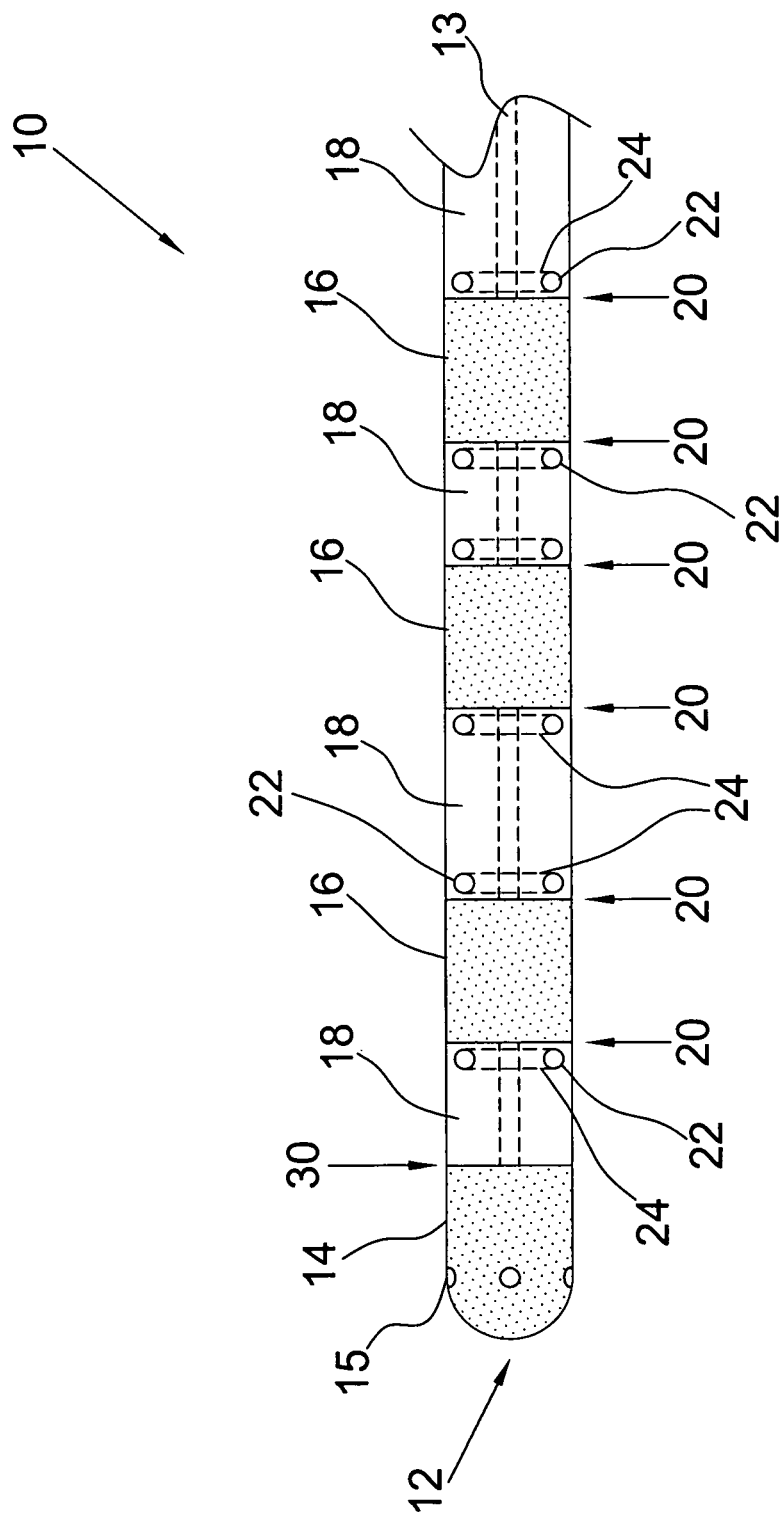
FIG. 1 is an elevational view of a distal portion of an irrigated ablation catheter according to an embodiment of the present invention.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment", "this embodiment", or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide apparatuses, methods and computer programs for ablation or denervation using an irrigated catheter device with multiple segmented ablation segments.

FIG. 1 is an elevational view of a distal portion of an irrigated ablation catheter 10 according to an embodiment of the present invention. The catheter 10 has an elongated body with a proximal end 124 (see FIG. 12), a distal end 12, and at least one fluid lumen 13 extending longitudinally therein. In the embodiment illustrated in FIG. 1, the fluid lumen 13 is defined by a lumen member (illustrated by longitudinally extending dashed lines in FIG. 1). A tip electrode 14 is disposed at the distal end 12. The tip electrode 14 may be an ablation tip electrode. The tip electrode 14 has irrigation holes 15 which are in fluid communication with the fluid lumen 13. In the distal portion, a plurality of segmented ablation electrodes 16 are spaced from the proximal end and the distal end 12 by electrically nonconductive segments 18, and they are spaced from each other longitudinally by electrically nonconductive segments 18 positioned intermediate the segmented ablation electrodes 16. The electrically nonconductive segments 18 may be made of a thermoplastic material. The segmented ablation electrodes 16 may be solid rings of a conductive material such as platinum, which are pressure fitted about the elongated body. For each segmented ablation electrode 16 that is longitudinally disposed next to one of the electrically nonconductive segments 18, an edge 20 is formed between an electrode end of the segmented ablation electrode 16 and a nonconductive segment end of the electrically nonconductive segment 18. A plurality of elution holes 22 are disposed adjacent to the edges 20. As used herein, "adjacent" to the edge 20 means very near or substantially abutting the edge 20, such that the distance between a specific elution hole 22 and the edge 20 to which it is "adjacent" is at least an order of magnitude smaller than the distance between that elution hole 22 and the next edge 20 or the distal end 12 or the proximal end of the elongated body. A plurality of ducts 24 establish fluid communication between the elution holes 22 and the fluid lumen 13. The tip electrode 14 has a proximal end which meets a nonconductive segment end of one of the electrically nonconductive segments 18 at a tip electrode edge 30. It is advantageous to be able to ablate with multiple irrigated electrodes 16 and tip electrode 14 to reduce the time needed to produce the ablation line on the tissue as compared to moving or dragging an ablation tip along the tissue.

In FIG. 1, the elution holes 22 are disposed in the electrically nonconductive segments 18. For each of the edges 20, at least one of the elution holes 22 is disposed adjacent the edge 20. In FIG. 1, multiple (e.g., four) elution holes 22 are spaced around a circumference adjacent the edge 20. The ducts 24 may be substantially perpendicular to the fluid lumen 13, as seen in FIG. 1. In alternative embodiments, the plurality of elution holes are disposed in the segmented ablation electrodes 16 or in both the segmented ablation electrodes 16 and the electrically nonconductive segments 18.

Figure 2:
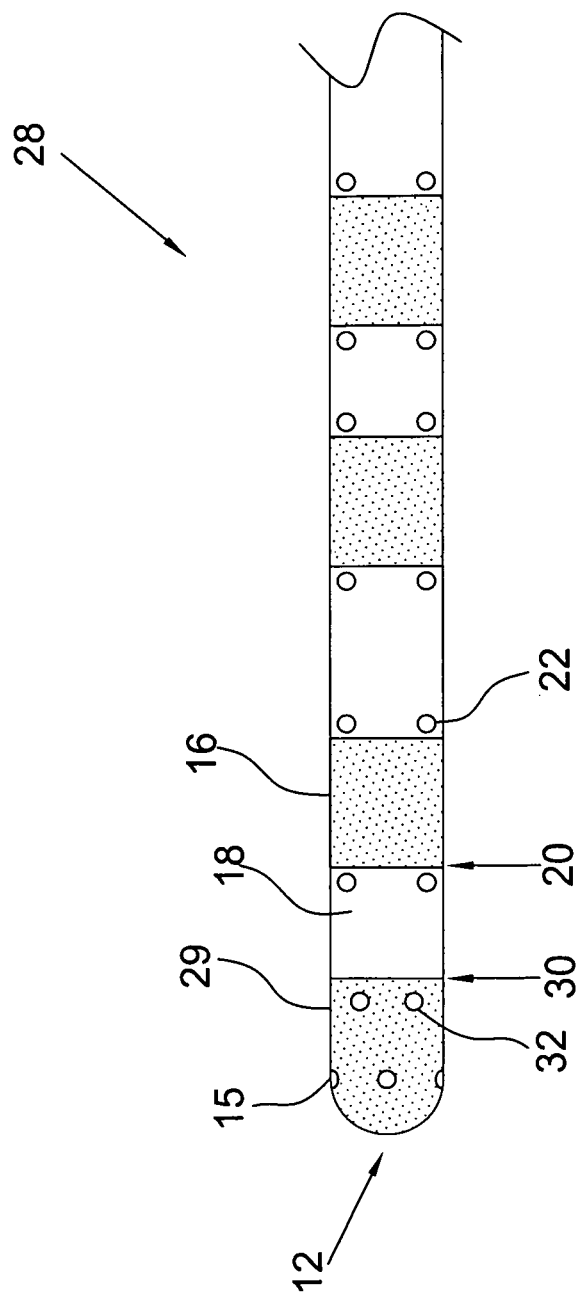
FIG. 2 is an elevational view of a distal portion of an irrigated ablation catheter according to an embodiment of the present invention.

FIG. 2 shows a distal portion of another irrigated ablation catheter 28 which is similar to the catheter 10 of FIG. 1. In FIG. 2, the tip electrode 29 has a proximal end which meets a nonconductive segment end of one of the electrically nonconductive segments 18 at a tip electrode edge 30. At least one tip electrode edge elution hole 32 is disposed adjacent to the tip electrode edge 30 and is in fluid communication with the fluid lumen 13 (see FIG. 1). In FIG. 2, the tip electrode edge elution holes 32 are spaced around a circumference adjacent the tip electrode edge 30, and are disposed in the tip electrode 29. In alternative embodiments, the tip electrode edge elution holes 32 may be disposed in the electrically nonconductive segment 18.

Figure 3:
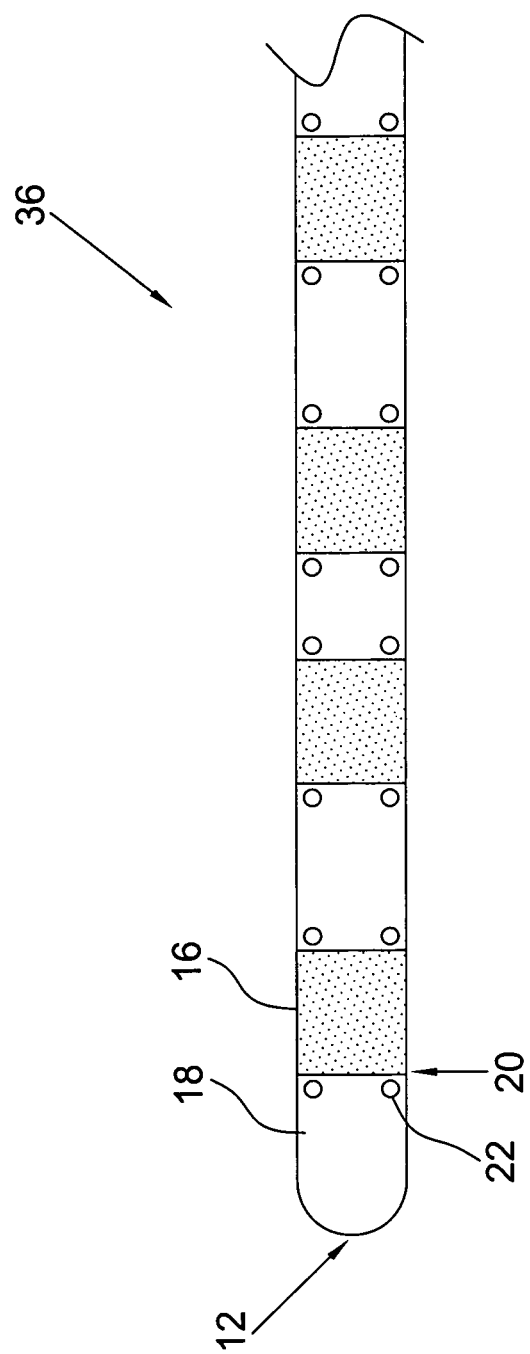
FIG. 3 is an elevational view of a distal portion of an irrigated ablation catheter according to an embodiment of the present invention.

FIG. 3 shows a distal portion of another irrigated ablation catheter 36 which is similar to the catheter 10 of FIG. 1 but does not have a tip electrode at the distal end 12.

Figure 4:
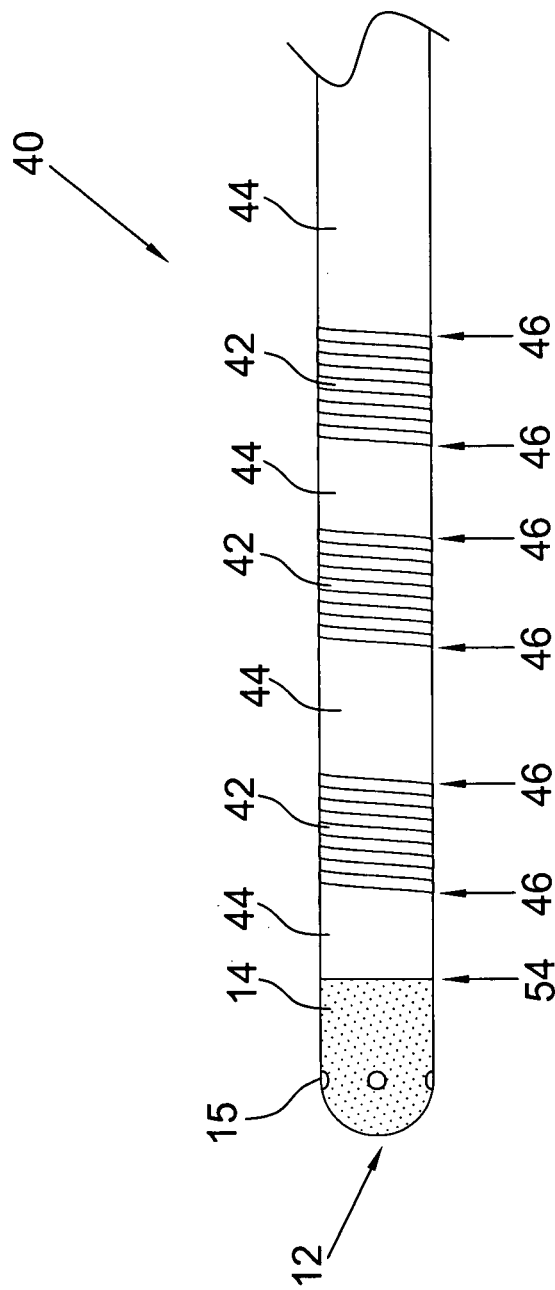
FIG. 4 is an elevational view of a distal portion of an irrigated ablation catheter according to an embodiment of the present invention.

FIG. 4 shows a distal portion of another irrigated ablation catheter 40 which is similar to the catheter 10 of FIG. 1. A tip electrode 14 is disposed at the distal end 12 and has irrigation holes 15. The segmented ablation electrodes in FIG. 4 are coil ring electrodes 42 which are spaced from the proximal end and the distal end 12 by electrically nonconductive segments 44, and the electrodes 42 are spaced from each other longitudinally by electrically nonconductive segments 44. An edge 46 is formed between an electrode end of the segmented ablation electrode 42 and a nonconductive segment end of the electrically nonconductive segment 44. The plurality of elution holes are disposed in the coil ring electrodes 42, which have gaps in the coil to allow fluid to flow out. For example, elution holes in fluid communication with the fluid lumen 13 via the ducts 24 (see FIG. 1) are provided in a portion of the elongated body underneath the coil ring electrodes 42, and the fluid flows through the elution holes and the gaps in the coil.

Figure 5:
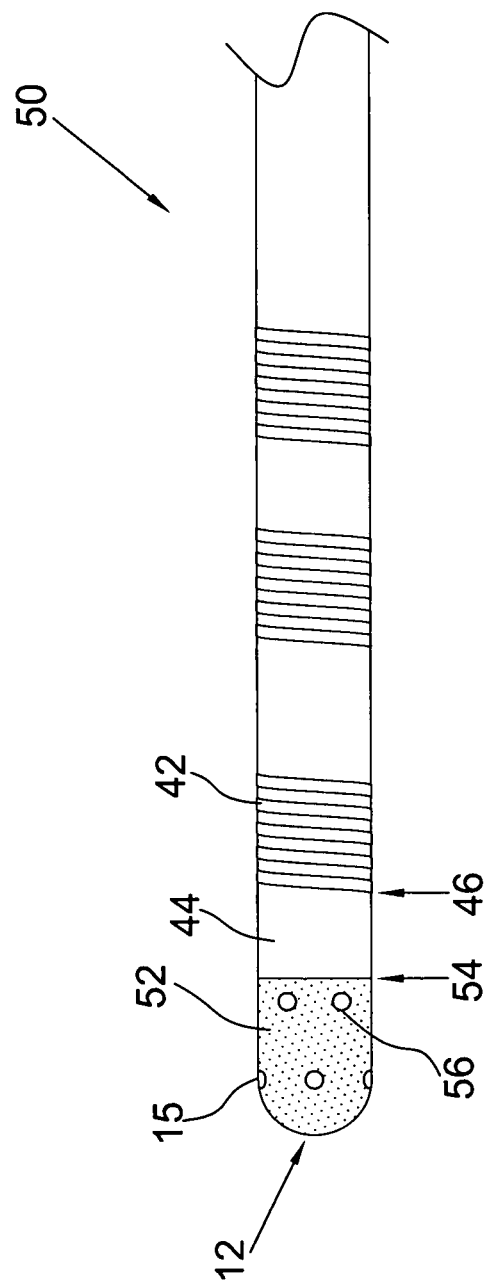
FIG. 5 is an elevational view of a distal portion of an irrigated ablation catheter according to an embodiment of the present invention.

FIG. 5 shows a distal portion of another irrigated ablation catheter 50 which is similar to the catheter 40 of FIG. 4. In FIG. 5, the tip electrode 52 has a proximal end which meets a nonconductive segment end of one of the electrically nonconductive segments 44 at a tip electrode edge 54. At least one tip electrode edge elution hole 56 is disposed adjacent to the tip electrode edge 54 and is in fluid communication with the fluid lumen 13 (see FIG. 1). In FIG. 5, the tip electrode edge elution holes 56 are spaced around a circumference adjacent the tip electrode edge 54, and are disposed in the tip electrode 52. In alternative embodiments, the tip electrode edge elution holes 56 may be disposed in the electrically nonconductive segment 44.

Figure 6:
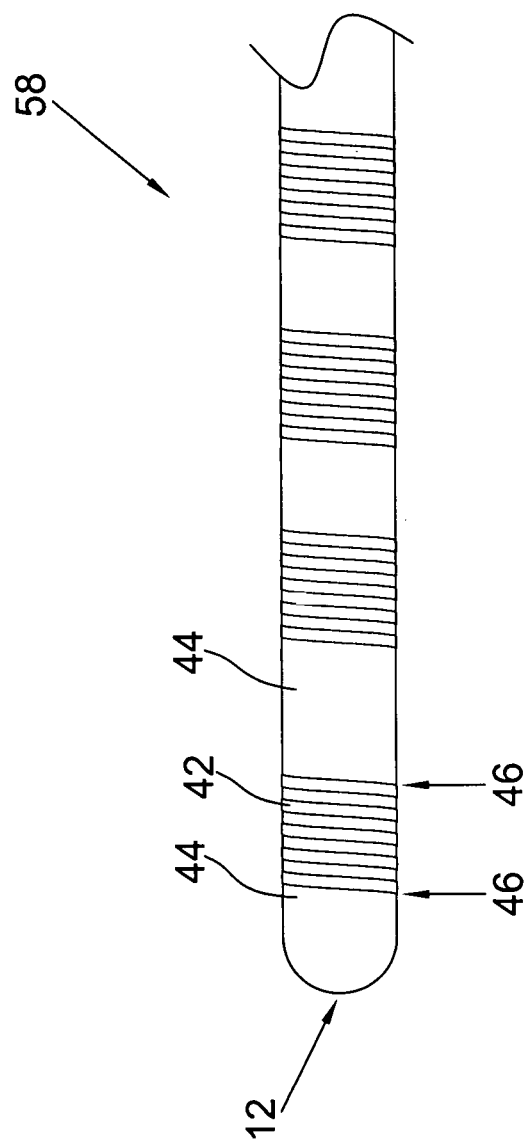
FIG. 6 is an elevational view of a distal portion of an irrigated ablation catheter according to an embodiment of the present invention.

FIG. 6 shows a distal portion of another irrigated ablation catheter 58 which is similar to the catheter 40 of FIG. 4 but does not have a tip electrode at the distal end 12.

Figure 7:
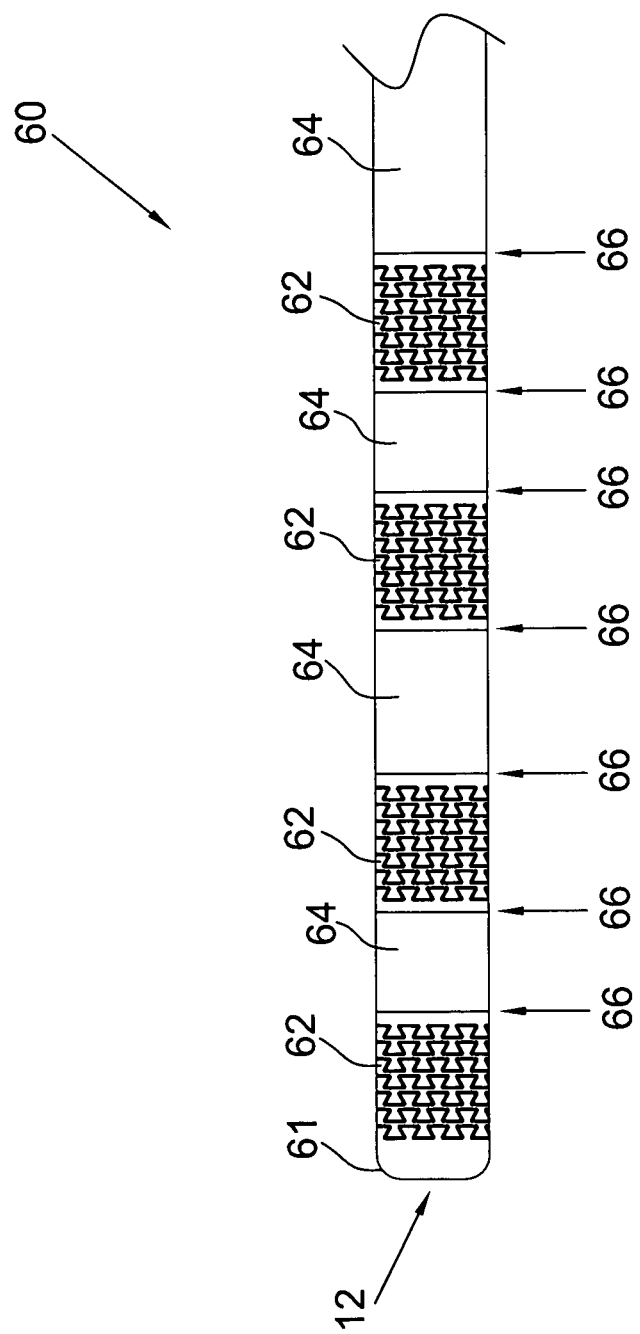
FIG. 7 is an elevational view of a distal portion of an irrigated ablation catheter according to an embodiment of the present invention.

FIG. 7 shows a distal portion of another irrigated ablation catheter 60 which is similar to the catheter 58 of FIG. 6 but has a tip electrode 61 at the distal end 12. Instead of the coil ring electrodes 42, the catheter 60 includes flexible ring electrodes 62 having gaps cut into a cylindrical sheet that forms a sidewall of the flexible ring electrodes 62 to allow fluid to flow out. One of the flexible ring electrodes 62 also forms the tip electrode 61. For example, elution holes in fluid communication with the fluid lumen 13 via the ducts 24 (see FIG. 1) are provided in a portion of the elongated body underneath the flexible ring electrodes 62, and the fluid flows through the elution holes and the gaps in the electrodes 62. The gaps may be laser cut into the cylindrical sheets of the electrodes 62. The flexible ring electrodes 62 are spaced from the proximal end of the elongated body by an electrically nonconductive segment 64, and the electrodes 62 are spaced from each other longitudinally by electrically nonconductive segments 64. An edge 66 is formed between an electrode end of the segmented ablation electrode 62 and a nonconductive segment end of the electrically nonconductive segment 64.

In FIG. 7, the gaps are elongated gaps in a corrugated pattern. As used herein, an elongated gap preferably has a length that is at least about 3 times the width of the gap, more preferably at least about 5 times, and most preferably at least about 10 times. A variety of gap patterns are possible. The gaps may be linear or curvilinear instead of corrugated. The gaps may be spiral gaps that extend in a helical pattern in the longitudinal direction or transverse gaps that are spaced from each other in the longitudinal direction. A transverse gap may extend less than 360 degrees or may extend the full 360 degrees. For a transverse gap that extends the full 360 degrees, some type of additional supporting structure is required to connect the severed-pieces together. For example, a biasing element such as an inner coil may be provided within the elongated body. Examples of flexible ring electrodes with elongated gaps can be found, for example, in US2008/0294158 and WO/2008/147599, the entire disclosures of which are incorporated herein by reference.

Figure 8:
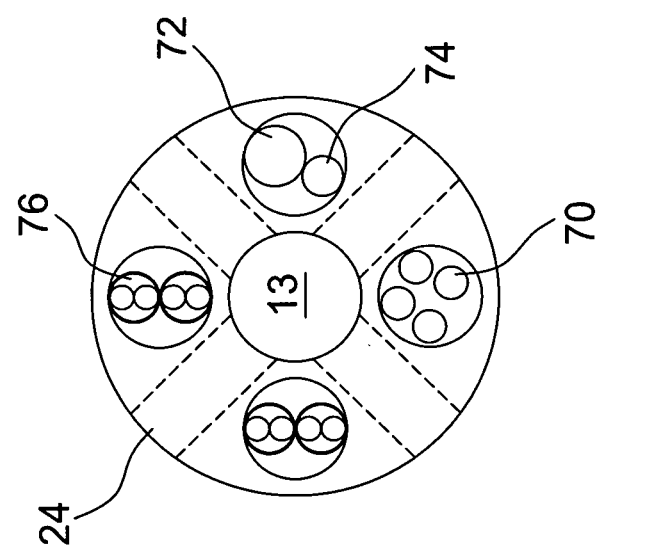
FIG. 8 is a transverse sectional view of a distal portion of an irrigated ablation catheter according to an embodiment of the present invention.

FIG. 8 is a transverse sectional view of a distal portion of an irrigated ablation catheter, which may be any of the catheters shown in FIGS. 1-7. FIG. 8 shows four ducts 24 connected to the fluid lumen 13. Additional lumens are provided for conducting wires 70 for supplying energy to the electrodes, one or more preshaping wires 72 made of a material such as Nitinol to provide a preformed shape for the distal portion of the catheter, one or more activation wires 74 for manipulating the distal portion (e.g., bidirectional bending and/or loop size adjusting), and a plurality of temperature sensor lines 76. The multiple lumens can be formed within a single extruded tubing to separate the fluid lumen 13 from the other lumens that house the various components described above.

Figure 9:
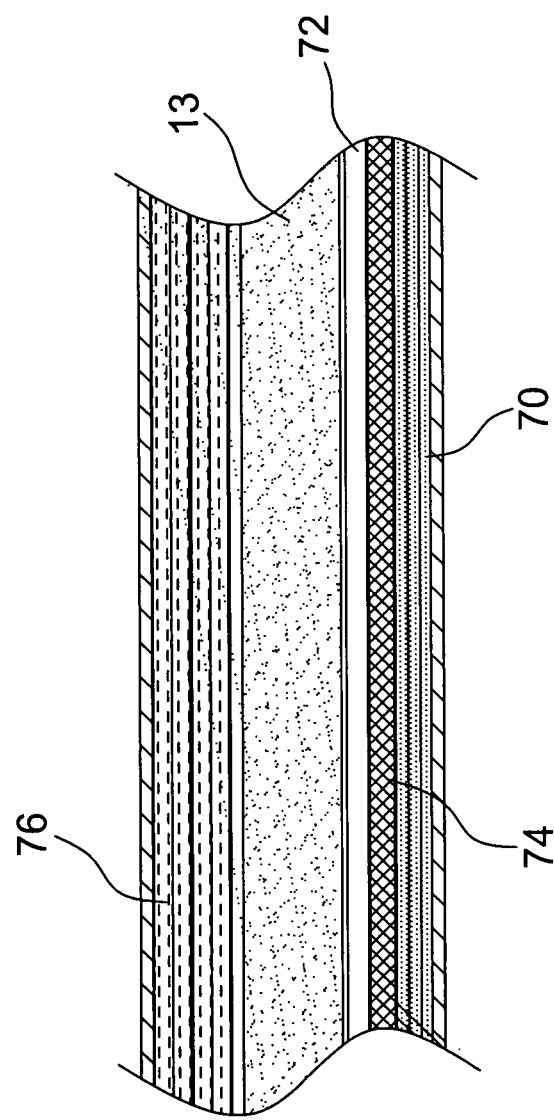
FIG. 9 is a longitudinal sectional view of a distal portion of an irrigated ablation catheter according to an embodiment of the present invention.

FIG. 9 is a longitudinal sectional view of a distal portion of an irrigated ablation catheter showing the fluid lumen 13, conducting wires 70, preshaping wires 72, activation wires 74, and temperature sensor lines 76.

Figure 10:
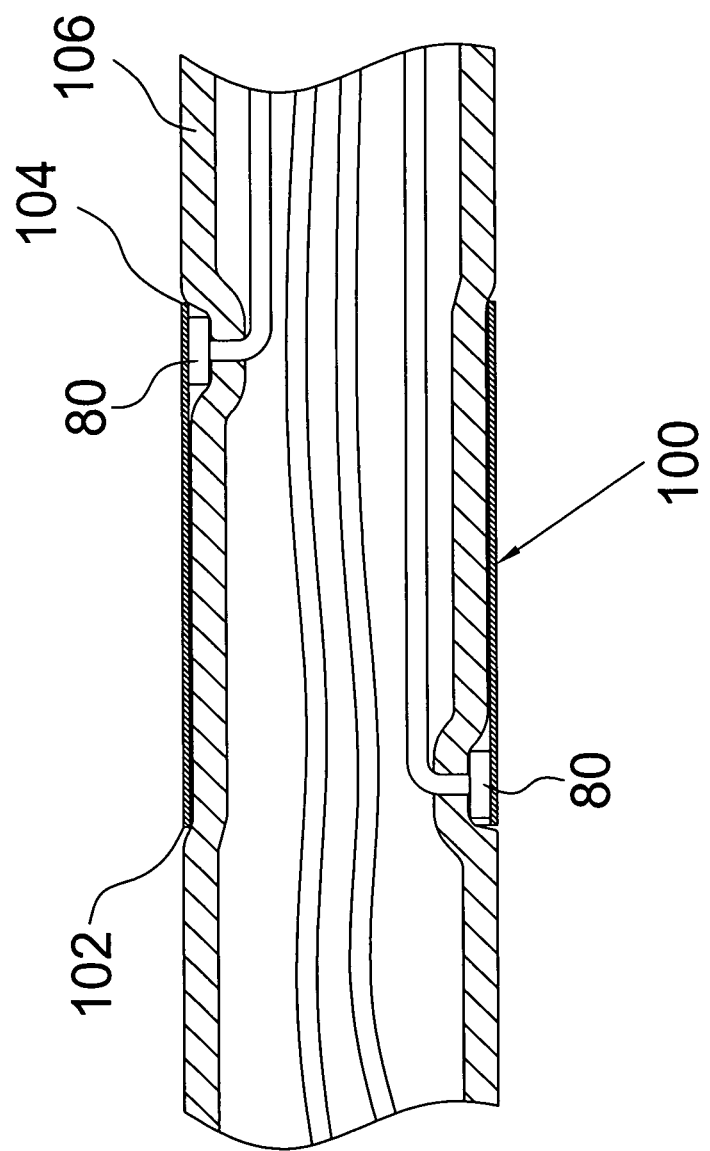
FIG. 10 is a longitudinal sectional view of a distal portion of an irrigated ablation catheter showing a temperature sensor located at an edge of an electrode according to an embodiment of the present invention.

FIG. 10 is a longitudinal sectional view of a distal portion of an irrigated ablation catheter showing temperature sensors 80 located at edges 102, 104 of an electrode 100. For clarity, elution holes and corresponding ducts are omitted in FIG. 10. The edges 102, 104 are where the electrode 100 abuts the underlying, electrically nonconductive support body 106. The temperature sensors 80 are disposed on and in contact with the segmented ablation electrode 100 at the electrode ends substantially abutting the edges 102, 104. For RF ablation, RF current densities are high at the edges 102, 104, because the electrically conductivity is discontinuous at the edges 102, 104. The resulting rise in current density at the electrode edges 102, 104 generates localized regions of increased power density and hence regions of higher temperatures. Therefore, temperature sensing and irrigation fluid cooling at the edges 102, 104 are desirable. In another embodiment, where a single temperature sensor 80 is used for an ablation electrode 100, the single temperature sensor 80 is disposed on and in contact with the ablation electrode 100 at a location situated between the edges 102 and 104. A temperature sensor may also be provided at the tip electrode (14, 29, 52, 61) adjacent the tip electrode edge (30, 54, 66) in the catheter (10, 28, 40, 50, 60) of FIG. 1, FIG. 2, FIG. 4, FIG. 5, or FIG. 7.

Figure 11:
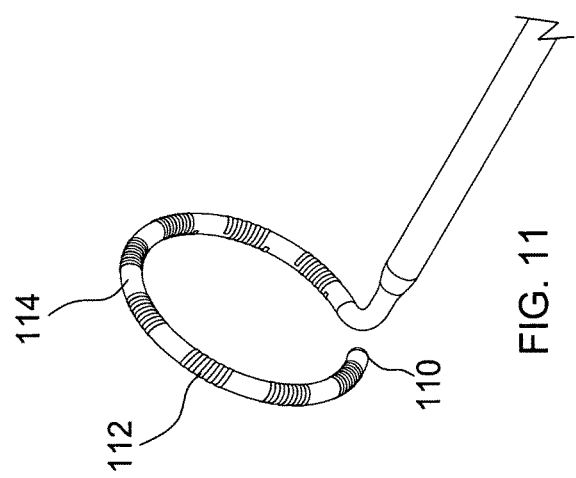
FIG. 11 is a perspective view of a distal portion of an irrigated ablation catheter having a preformed loop shape.

FIG. 11 is a perspective view of a distal portion of an irrigated ablation catheter having a preformed loop shape. For example, the one or more preshaping wires 72 includes a material such as Nitinol so that the distal portion is preformed into a substantially closed loop with the distal tip 110 having a plurality of longitudinally spaced segmented ablation electrodes 112 and electrically nonconductive segments 114.

Figure 12:
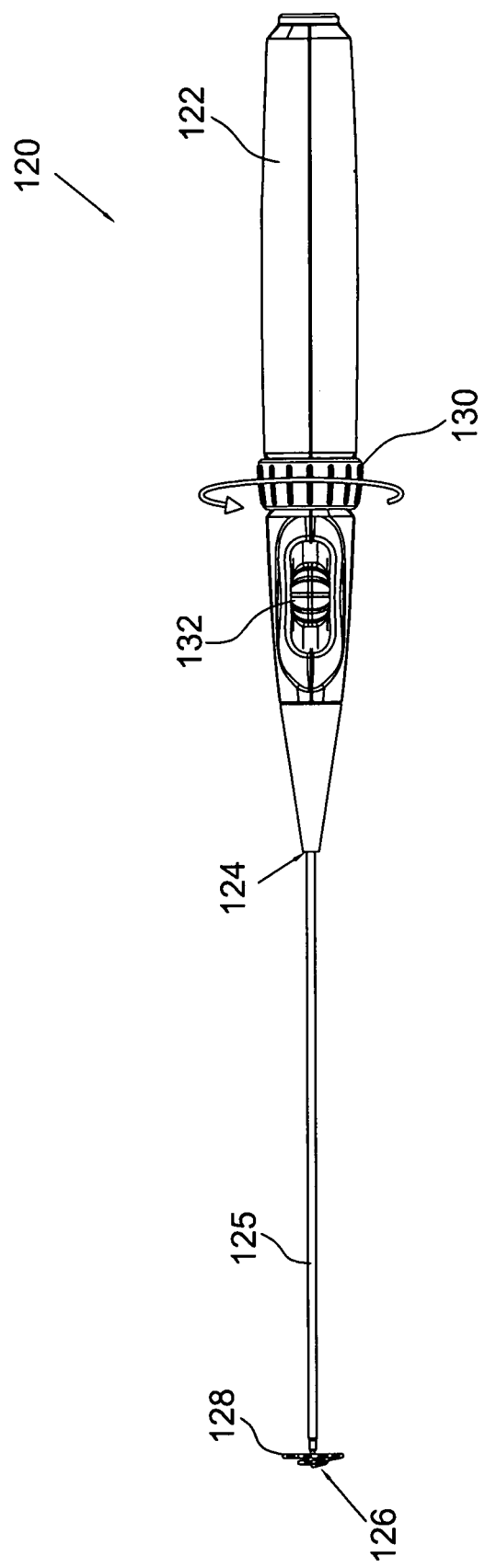
FIG. 12 is an elevational view of an irrigated ablation catheter showing a handle for manipulating the shape of a distal portion of the catheter.
Figure 13:
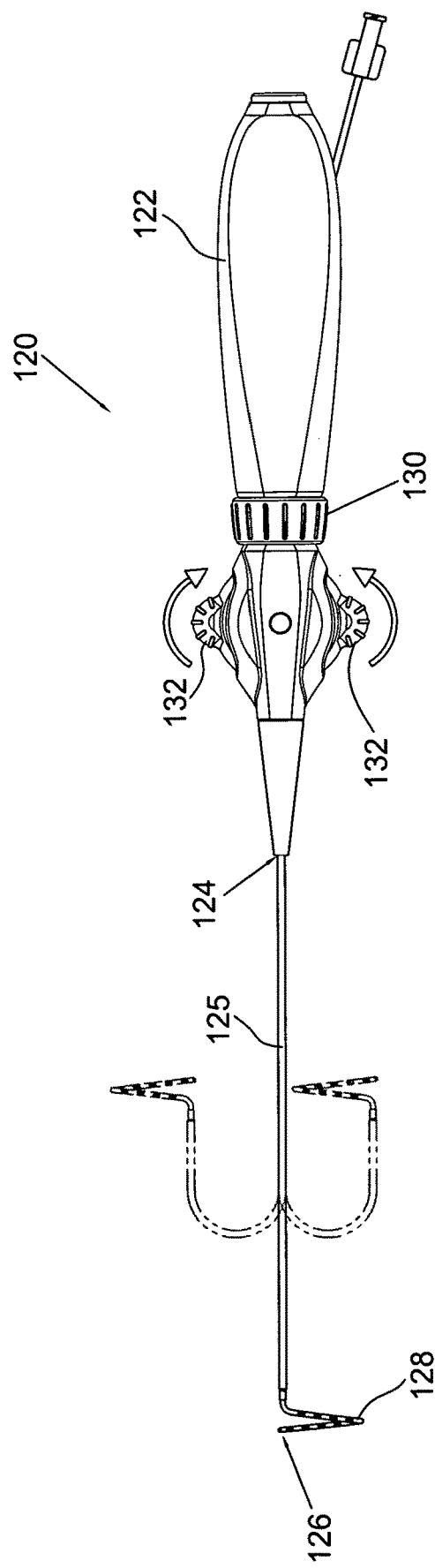
FIG. 13 is another elevational view of the irrigated ablation catheter of FIG. 12.

FIGS. 12 and 13 are elevational views of an irrigated ablation catheter 120 showing a handle 122 connected to a proximal end 124 of the elongated body 125 for manipulating the shape of a distal portion of the catheter 120 near the distal end 126. In FIG. 12, the distal portion of the catheter 120 includes a loop 128 having segmented ablation electrodes (see FIG. 11). The handle 122 includes a first roller 130 for changing the size of the loop 128, and a second set of rollers or sliders 132 for bidirectional bending of the elongated body 125.

Figure 14:
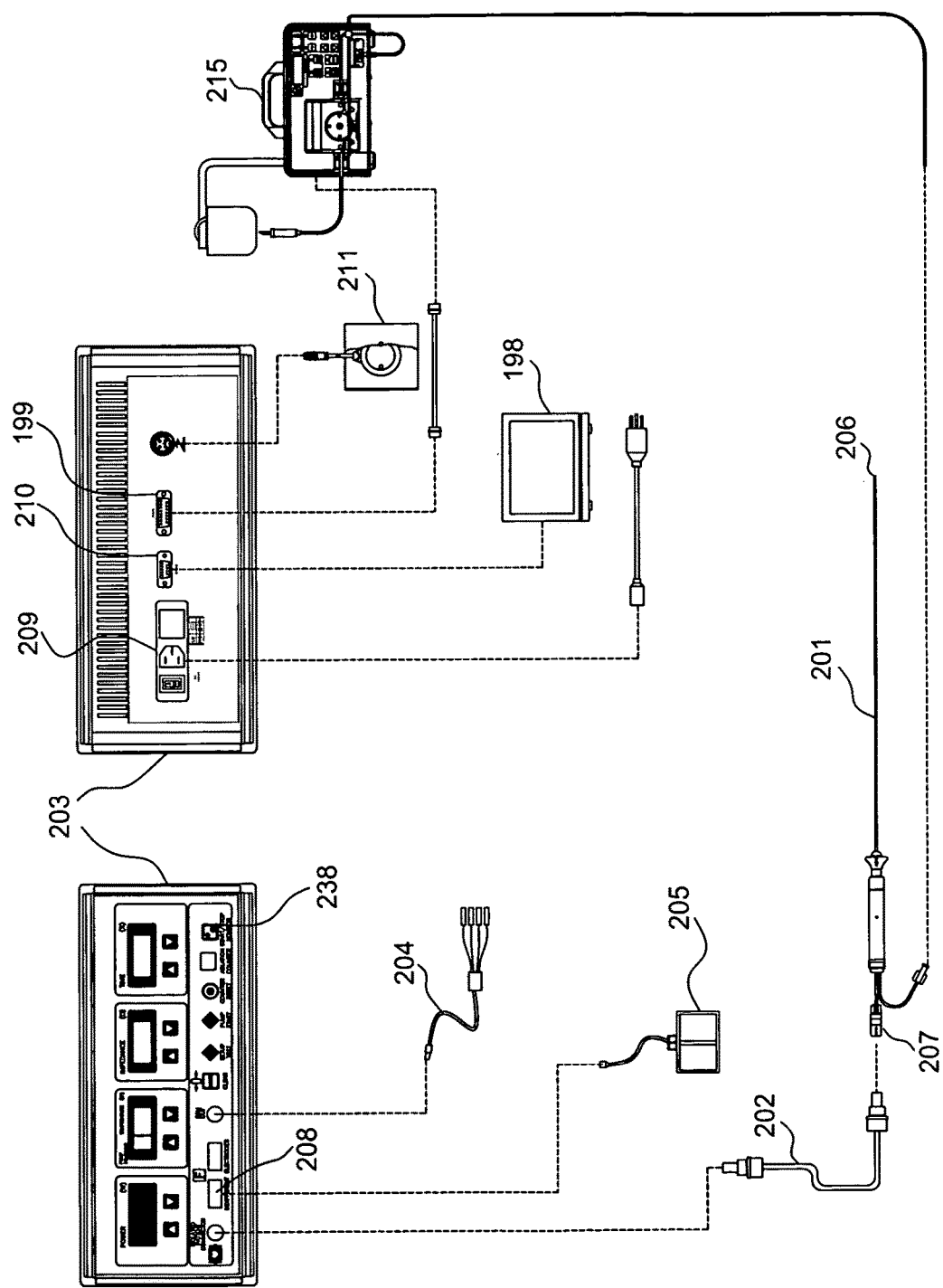
FIG. 14 is a system installation diagram of an RF ablation system with an irrigated ablation catheter.

FIG. 14 is a system installation diagram of an RF ablation system with an irrigated ablation catheter. The system includes a catheter 201 with multiple electrodes, a connecting cable 202, an RF generator 203, an EKG connecting cable 204, and a DIP (Dispersive Indifferent Patch) electrode device 205 that is connected to the RF generator 203 through an isolated patient connector 208. The DIP electrode device 205 is placed under a patient, during an ablation procedure, to provide a closed-loop circuit of the RF energy delivery system. The catheter 201 has a plurality of electrodes 206 and a plurality of temperature sensing elements. Each temperature sensing element is located at the proximity of each of the electrodes 206. The catheter 201 is connected to the RF generator 203 through the connecting cable 202. Each of the insulated temperature wires and the conducting wires of the catheter 201 are secured to a connector 207 contact pin of the catheter 201. Therefore, the measured temperature data from each of the multiple electrodes is relayed to a control mechanism located in the CPU board 214 (FIG. 15) of the RF generator 203. In the meantime, the RF energy output is delivered through each of the conducting wires to a respective individual electrode on the catheter 201. The control mechanism of the CPU board 214 also controls the operation of an irrigation pump 215 which is used to pump irrigation fluid to the irrigated catheter 201.

The EKG connecting cable 204 is used to transmit the intracardiac electrical signal to an external EKG monitor 220 (FIG. 15) to display the intracardiac electrical signal sensed and returned by each of the electrodes 206. At the back panel of the RF generator 203, there are a power supply port 209, a data output port 210, and a pump port 199. An optional footswitch 211 is also provided for the user's convenience. Either the footswitch 211 or a button 238 on the front panel of the RF generator 203 can be used to start and stop the RF energy delivery.

Figure 15:
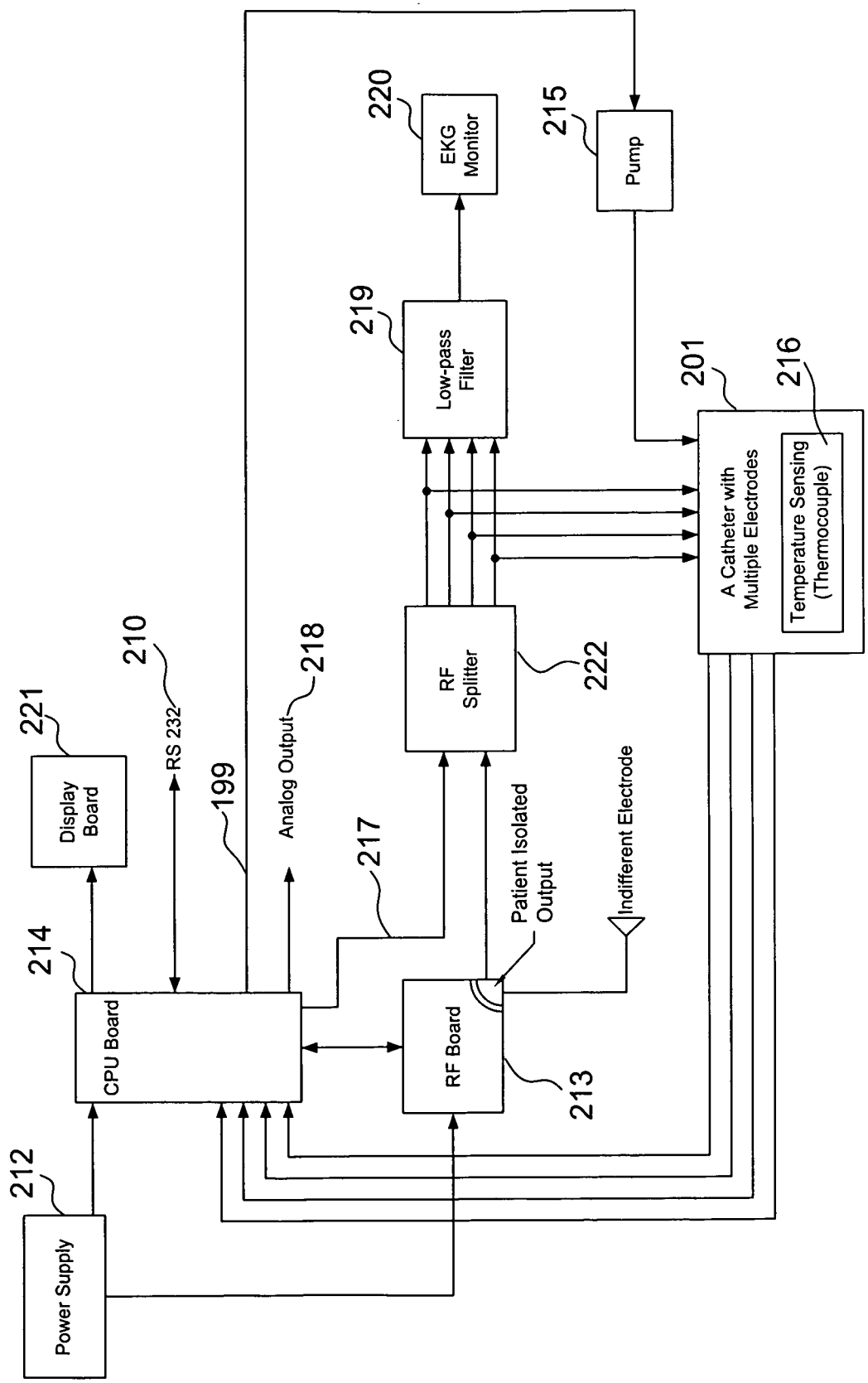
FIG. 15 is a block diagram of the RF ablation system of FIG. 14.

FIG. 15 is a block diagram of the RF ablation system of FIG. 14, to provide RF energy delivery through an RF splitter to each of the multiple electrodes of the ablation catheter 201. The power supply source 212 is connected to the RF generator 203 having the RF board 213 and the CPU board 214. A software program becomes an integral portion of the CPU board 214. A catheter 201 that has multiple electrodes has a plurality of temperature sensing elements 216. Each temperature sensing element 216 is associated with one of the electrodes 206. The measured temperature data is relayed to the software program inside the CPU board 214. The data from the CPU board 214, such as power, temperature, impedance, and time, is then displayed via a display board 221. The command or instruction is issued from the CPU board 214 to the RF board 213 to control the RF energy output. An RF splitter 222 is employed to split the RF energy in order to deliver it to one or more of the conducting wires, wherefrom thereafter the RF energy output is relayed to the corresponding electrode or electrodes. A digital control signal 217 from the CPU board 214 to the RF splitter 222 controls the manner in which the RF energy is delivered to the one or more conducting wires. The RF energy may be delivered in an independent manner, or a sequential manner, or a simultaneous manner. The conducting wires which deliver the RF energy to the multiple electrodes of the catheter 201 also carry a low-frequency EKG signal which is sensed and returned by each of the multiple electrodes. A low-pass filter 219 is used to allow only the EKG signal to pass to the EKG monitor 220 for real-time display. The control mechanism of the catheter system only allows ablation or denervation when the real-time cardiac electrical signal assures that the catheter is still at a proper location. Data can be stored in the CPU 214 or outputted through an RS232 port 210 to an external computer 198 for data analysis. Data may also be outputted to an analog output port 218. The CPU board 214 sends a control signal via the pump port 199 to the pump 215 to control the operation of the pump 215, such as, for example, the flow rate of the fluid delivered by the pump 215 to the irrigated catheter 201.

Figure 16:
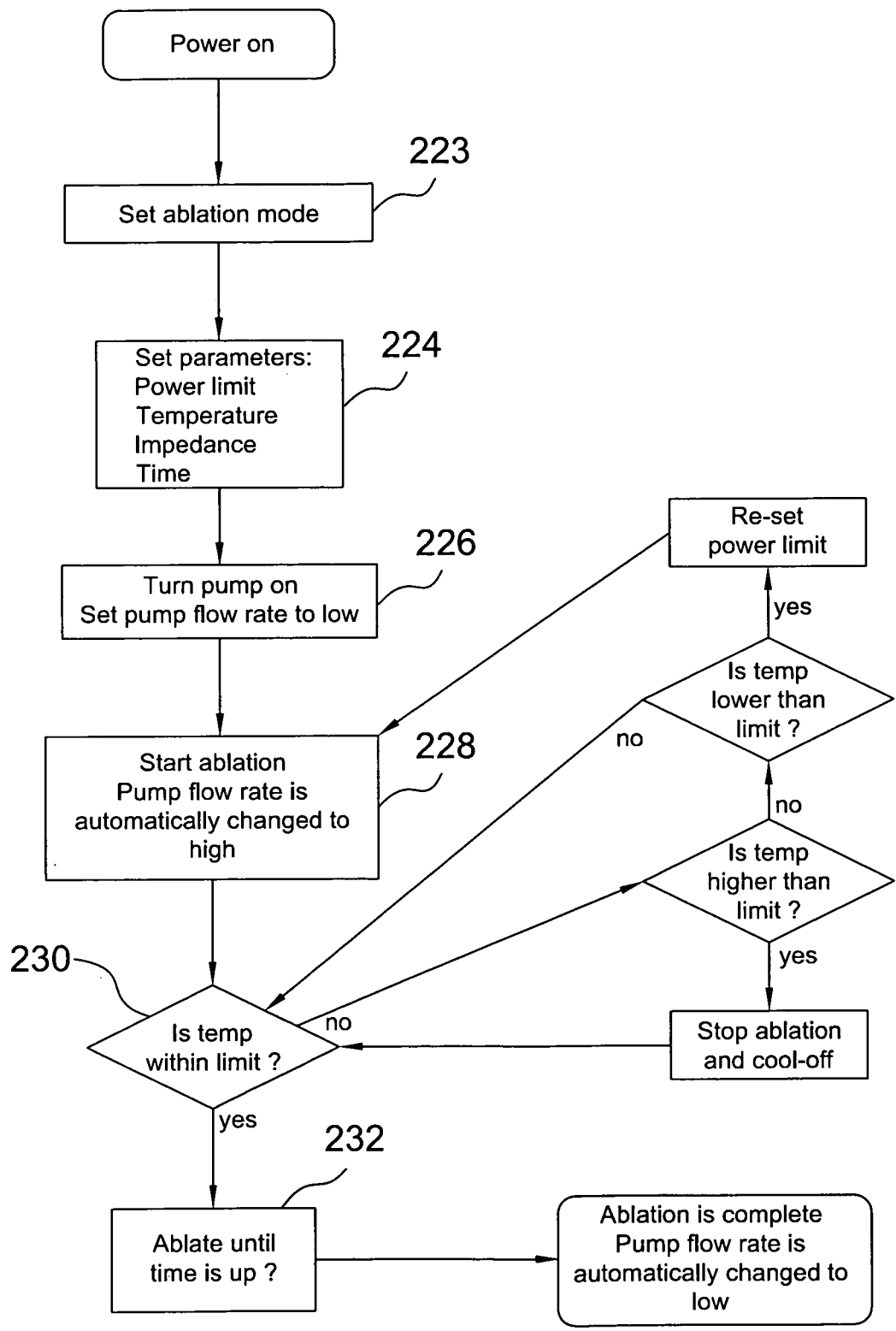
FIG. 16 is a flow diagram of the software program for the RF ablation system of FIG. 14.

FIG. 16 is a flow diagram of the software program for the RF ablation system of FIG. 14. The major steps in the software program include: "Set ablation mode" block 223, "Set parameters" block 224, "Turn pump on" block 226, "Start ablation" block 228, "Is temp within limit?" block 230 and "Ablate until time is up" block 232. The ablation mode 223 includes one of the modes: a simultaneous mode, a sequential mode, a random-order mode, or a combination of the above. The "Set parameters" block 224 includes setting the power limit, the temperature limit, the impedance limit, and the time limit. The power limit 224 is initially set at a relatively low value for safety reasons. An example would be to set the initial power limit at 15 watts. The power limit can be raised in appropriate increments until a final power limit of the RF generator is reached. One example for the final power limit would be 150 watts. The temperature limit is set for a range, which is appropriate for the ablative lesion. One example would be to set the ablation temperature limit as 67.5° C.±2.5° C. The "time is up" is a predetermined time duration for ablating any of the electrodes. One example would be to set the time limit for electrode no. 1 as 30 seconds. More details of operating the system can be found in U.S. Pat. No. 5,954,719, which is incorporated herein by reference in its entirety. When the pump is turned on (block 226), the pump flow rate is set to low. When the ablation is started (block 228), the pump flow rate is automatically changed to high. When the ablation is complete, the pump flow rate is automatically changed to low.

The RF energy may be unipolar RF energy or bipolar RF energy depending on the configuration. The control mechanism or controller on the CPU board 214 of the RF generator 203 is configured to control the energy source to supply energy to the plurality of segmented ablation electrodes in an independent manner (control energy to each electrode independently), a sequential manner (control energy to the electrodes in a preset sequence), or a simultaneous manner (control energy to the electrodes simultaneously). The controller may be configured to control the energy source to supply energy to the segmented ablation electrodes based on signals received from the temperature sensors so as to control temperatures of the segmented ablation electrodes. Controlling the temperatures of the electrodes by regulating the supply of energy to the electrodes is also described, for instance, in U.S. Pat. No. 6,346,104, which is incorporated herein by reference in its entirety.

Figure 17:
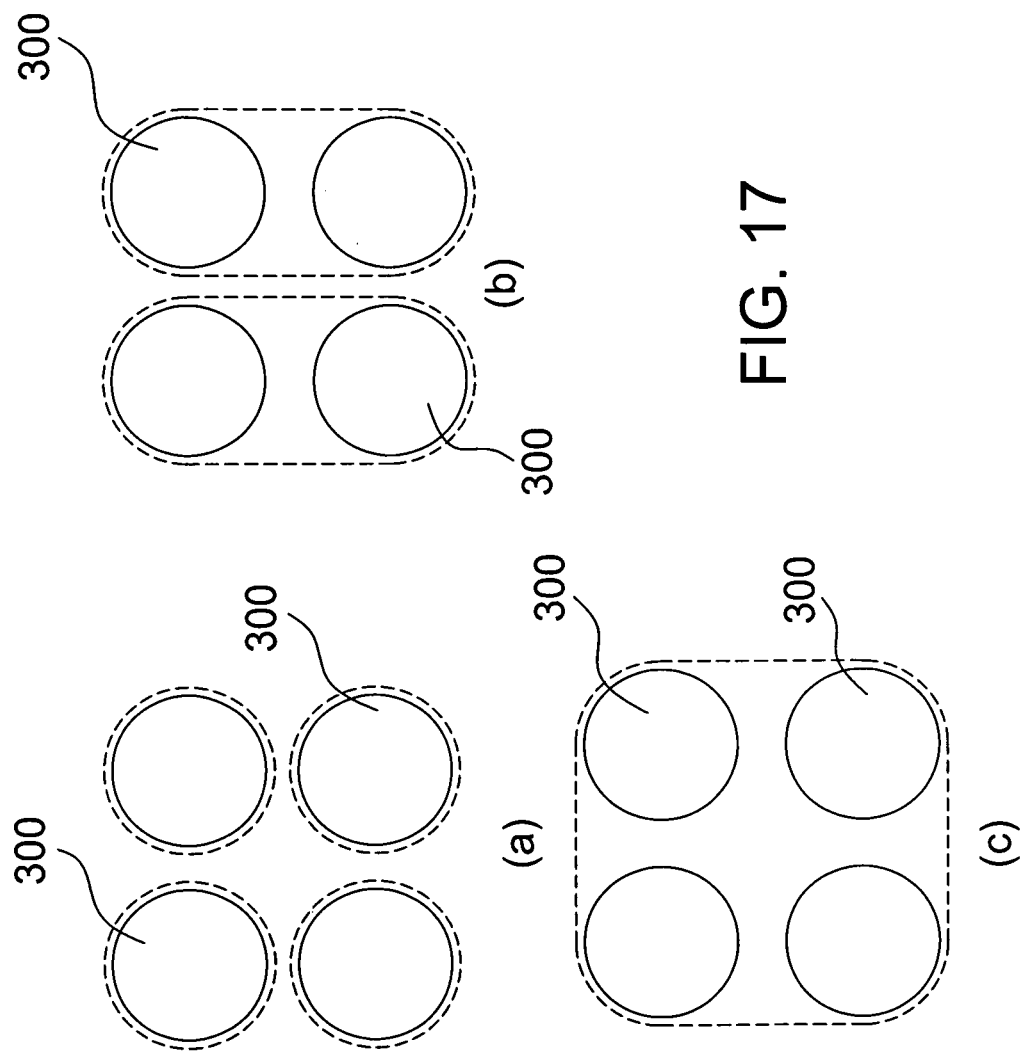
FIG. 17 shows schematic diagrams of ablation patterns around at least one vessel ostium.

FIG. 17 shows schematic diagrams of ablation patterns around at least one vessel ostium 300. The loop 128 of the catheter in FIG. 12 can be placed around at least one vessel ostium in a chamber of a patient to ablate the tissue on a chamber wall of the chamber around the at least one vessel ostium. FIG. 17(a) shows an ablation pattern around each vessel ostium 300. FIG. 17(b) shows an ablation pattern around two vessel ostia 300. FIG. 17(c) shows an ablation pattern around four vessel ostia 300. Each vessel ostium may be a pulmonary vein for pulmonary vein isolation. See, e.g., U.S. Pat. No. 6,325,797, which is incorporated herein by reference in its entirety. Another application is for ablating renal sympathetic nerves in therapeutic renal sympathetic denervation to achieve reductions of blood pressure in patients suffering from renal sympathetic hyperactivity associated with hypertension and its progression. See, e.g., Henry Krum et al., Catheter-Based Renal Sympathetic Denervation for Resistant Hypertension: A Multicentre Safety and Proof-of-Principle Cohort Study, published online Mar. 30, 2009 at www.thelancet.com. The catheter will be sized differently for ablating or denervating nerves located within and around different vessels and walls. For example, the size of the catheter for ablating renal sympathetic nerves is typically smaller than that for ablating around a pulmonary vein.

In the description, numerous details are set forth for purposes of explanation in order to provide a thorough understanding of the present invention. However, it will be apparent to one skilled in the art that not all of these specific details are required in order to practice the present invention. It is also noted that the invention may be described as a process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged.

From the foregoing, it will be apparent that the invention provides methods, apparatuses and programs stored on computer readable media for ablation using an irrigated catheter device with multiple segmented ablation segments. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A catheter comprising:
    an elongated body comprising a proximal portion and a distal portion, the distal portion including a distal end and a fluid lumen;
    a handle connected to the proximal portion;
    a plurality of flexible electrode segments positioned at the distal portion; and
    a plurality of intermediate segments;
    wherein the plurality of flexible electrode segments and the plurality of intermediate segments alternate longitudinally along the distal portion such that each pair of adjacent flexible electrode segments of the plurality of flexible electrode segments are spaced from each other longitudinally by a respective one of the plurality of intermediate segments, each flexible electrode segment of the plurality of flexible electrode segments extending longitudinally from a first end to a second end, wherein for a first flexible electrode segment of the plurality of flexible electrode segments that is longitudinally disposed between first and second adjacent intermediate segments of the plurality of intermediate segments, a first edge is formed between the first end of the first flexible electrode segment and an end of the first intermediate segment and a second edge is formed between the second end of the first flexible electrode segment and an end of the second intermediate segment, and wherein a plurality of elution holes are disposed on the first intermediate segment adjacent the first edge and on the second intermediate segment adjacent the second edge such that, for any one of the plurality of elution holes, a distance between the any one of the plurality of elution holes and the adjacent one of the first and second edge is at least an order of magnitude smaller than a distance between the any one of the plurality of elution holes and the non-adjacent one of the first and second edge, and wherein the distal portion is preformed into a substantially closed loop, and the handle is configured to change the size of the loop.

2. The catheter in accordance with claim 1, wherein the respective one of the plurality of intermediate segments comprises a nonconductive member.

3. The catheter in accordance with claim 1, further comprising a lumen member, the lumen member extending at least partially through the distal portion, wherein the fluid lumen is defined by the lumen member.

4. The catheter in accordance with claim 3, wherein the lumen member includes a plurality of openings extending therethrough.

5. The catheter in accordance with claim 1, wherein the distal portion comprises at least one sensor located at the edge.

6. The catheter in accordance with claim 5, wherein the sensor comprises a physiologic sensor.

7. The catheter in accordance with claim 1, wherein each flexible electrode segment of the plurality of flexible electrode segments further comprises a substantially cylindrical sidewall provided with at least one elongated gap selected from the group consisting of an annular gap around a portion of a circumference of the sidewall and a helical gap forming a helical pattern on the sidewall.

8. The catheter in accordance with claim 1, wherein each flexible electrode segment of the plurality of flexible electrode segments further comprises a substantially cylindrical sidewall provided with at least one elongated gap formed at least partially therethrough, the at least one elongated gap extending as one or more of an annular gap around a portion of a circumference of the sidewall, a helical gap forming a helical pattern on the sidewall, and a gap that outlines alternating interlocking blocks.

9. The catheter in accordance with claim 1, wherein each flexible electrode segment of the plurality of flexible electrode segments comprises a sidewall, and at least one elongated gap extends entirely through the sidewall.

10. The catheter in accordance with claim 9, further comprising a biasing member that resiliently biases the sidewall to a pre-determined configuration.

11. The catheter in accordance with claim 1, wherein each flexible electrode segment of the plurality of flexible electrode segments comprises a sidewall, and wherein the sidewall comprises a spiraling stem defining opposing interlocking blocks.

12. The catheter in accordance with claim 11, wherein the sidewall further comprises alternating interlocking blocks disposed on opposite sides of at least one elongated gap, each of the alternating interlocking blocks comprising a head and a neck, the head being wider than the neck.

13. The catheter in accordance with claim 12, wherein the sidewall further comprises a second stem, wherein a first head, comprising a first neck connected to a first stem, is disposed between second and third heads, wherein the second head has a second neck and the third head has a third neck, wherein the second and third necks are connected to the second stem, and wherein the second and third heads have a distance between them that is shorter than a widest width of the first head.

14. The catheter in accordance with claim 9, wherein the at least one elongated gap defines a corrugated pattern.

15. The catheter in accordance with claim 1, wherein the respective one of the plurality of intermediate segments is shorter than the adjacent flexible electrode segments of the plurality of flexible electrode segments.

16. A distal portion for a catheter, the distal portion comprising:
a distal end;
a fluid lumen;
a plurality of flexible electrode segments; and
a plurality of intermediate segments;
wherein the plurality of flexible electrode segments and the plurality of intermediate segments alternate longitudinally along the distal portion such that each pair of adjacent flexible electrode segments of the plurality of flexible electrode segments are spaced from each other longitudinally by a respective one of the plurality of intermediate segments, each flexible electrode segment of the plurality of flexible electrode segments extending longitudinally from a first end to a second end, wherein the respective one of the plurality of intermediate segments is shorter than the adjacent flexible electrode segments of the plurality of flexible electrode segments, wherein for a first flexible electrode segment of the plurality of flexible electrode segments that is longitudinally disposed between first and second adjacent intermediate segments of the plurality of intermediate segments, a first edge is formed between the first end of the first flexible electrode segment and an end of the first intermediate segment and a second edge is formed between the second end of the first flexible electrode segment and an end of the second intermediate segment, and wherein a plurality of elution holes are disposed on the first intermediate segment adjacent the first edge and on the second intermediate segment adjacent the second edge such that, for any one of the plurality of elution holes, a distance between the any one of the plurality of elution holes and the adjacent one of the first and second edge is at least an order of magnitude smaller than a distance between the any one of the plurality of elution holes and the non-adjacent one of the first and second edge, and wherein the distal portion is preformed into a substantially closed loop that is configured to change size.

17. The distal portion in accordance with claim 16, wherein the plurality of flexible electrode segments are biased to a predetermined configuration.

18. The distal portion in accordance with claim 16, wherein at least one elongated gap extends about each flexible electrode segment of the plurality of flexible electrode segments in a helical pattern.

19. The distal portion in accordance with claim 16, wherein the plurality of flexible electrode segments comprise at least one stem and opposing blocks extending transversely from the stem.

20. The distal portion in accordance with claim 16, wherein the respective one of the plurality of intermediate segments comprises a nonconductive member.

21. The distal portion in accordance with claim 16, further comprising a lumen member, the lumen member extending at least partially through the distal portion, wherein the fluid lumen is defined by the lumen member.

22. The distal portion in accordance with claim 16, wherein at least one elongated gap extends entirely through each flexible electrode segment of the plurality of flexible electrode segments.

23. The distal portion in accordance with claim 16, further comprising at least one biasing member that resiliently biases the plurality of flexible electrode segments to a pre-determined configuration.

24. The distal portion in accordance with claim 16, wherein the plurality of flexible electrode segments comprise alternating interlocking blocks disposed on opposite sides of the at least one elongated gap, each of the alternating interlocking blocks comprising a head and a neck, the head being wider than the neck.

25. The distal portion in accordance with claim 24, wherein a first head of a first of the alternating interlocking blocks is disposed between a second neck of a second of the alternating interlocking blocks and a third neck of a third of the alternating interlocking blocks, wherein the first head has a first neck, the second head has a second neck and the third head has a third neck, and wherein the second and third heads have a distance between them that is shorter than a widest width of the first head.

26. A catheter comprising:
an elongated body comprising a fluid lumen, a distal portion and a proximal portion;
a handle connected to the proximal portion;
a plurality of flexible electrodes positioned at the distal portion, each flexible electrode of the plurality of flexible electrodes extending longitudinally from a first end to a second end; and
a plurality of intermediate nonconductive segments, wherein the plurality of flexible electrode segments and the plurality of intermediate nonconductive segments alternate longitudinally along the distal portion such that each pair of adjacent flexible electrodes of the plurality of flexible electrodes are spaced from each other longitudinally by a respective one of the plurality of intermediate nonconductive segments, wherein for a first flexible electrode of the plurality of flexible electrodes that is longitudinally disposed between first and second adjacent intermediate nonconductive segments of the plurality of intermediate nonconductive segments, a first edge is formed between the first end of the first flexible electrode segment and an end of the first intermediate nonconductive segment and a second edge is formed between the second end of the first flexible electrode segment and an end of the second intermediate nonconductive segment, and wherein a plurality of elution holes are disposed on the first intermediate nonconductive segment adjacent the first edge and on the second intermediate nonconductive segment adjacent the second edge such that, for any one of the plurality of elution holes, a distance between the any one of the plurality of elution holes and the adjacent one of the first and second edge is at least an order of magnitude smaller than a distance between the any one of the plurality of elution holes and the non-adjacent one of the first and second edge, and wherein the distal portion is preformed into a substantially closed loop and the handle is configured to change the size of the loop.

* * * * *